(12) United States Patent
Ehlis et al.

(10) Patent No.: US 10,119,039 B2
(45) Date of Patent: Nov. 6, 2018

(54) USE OF 2-(2-HYDROXYPHENYL)BENZOTRIAZOLE COMPOUNDS AS AN UV ABSORBING AGENT IN COATINGS

(71) Applicant: BASF SE, Ludwigshafen (DE)

(72) Inventors: Thomas Ehlis, Freiburg (DE);
Adalbert Braig, Binzen (DE);
Wolfgang Peter, Altlussheim (DE);
Ruediger Hainz, Binzen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/026,085

(22) PCT Filed: Oct. 23, 2014

(86) PCT No.: PCT/EP2014/072700
§ 371 (c)(1),
(2) Date: Mar. 30, 2016

(87) PCT Pub. No.: WO2015/062946
PCT Pub. Date: May 7, 2015

(65) Prior Publication Data
US 2016/0215151 A1    Jul. 28, 2016

(30) Foreign Application Priority Data

Oct. 29, 2013 (EP) .................... 13190563

(51) Int. Cl.
| | | |
|---|---|---|
| C08K 5/00 | (2006.01) | |
| C09D 7/12 | (2006.01) | |
| C08K 5/3435 | (2006.01) | |
| C08K 5/3475 | (2006.01) | |
| C09D 4/00 | (2006.01) | |
| C09D 133/06 | (2006.01) | |
| C08G 18/62 | (2006.01) | |
| C08G 18/78 | (2006.01) | |
| C09D 175/04 | (2006.01) | |
| C07D 249/20 | (2006.01) | |
| C09D 5/00 | (2006.01) | |
| C09D 7/48 | (2018.01) | |
| C08K 5/3492 | (2006.01) | |

(52) U.S. Cl.
CPC ......... *C09D 7/1241* (2013.01); *C07D 249/20* (2013.01); *C08G 18/6225* (2013.01); *C08G 18/7831* (2013.01); *C08K 5/3435* (2013.01); *C08K 5/3475* (2013.01); *C09D 4/00* (2013.01); *C09D 5/00* (2013.01); *C09D 7/48* (2018.01); *C09D 133/06* (2013.01); *C09D 175/04* (2013.01); *C08K 5/34926* (2013.01)

(58) Field of Classification Search
None
See application file for complete search history.

(56) References Cited

U.S. PATENT DOCUMENTS

| | | |
|---|---|---|
| 3,213,058 A | 10/1965 | Boyle et al. |
| 4,315,509 A | 2/1982 | Smit |
| 4,325,863 A | 4/1982 | Hinsken et al. |
| 4,338,244 A | 7/1982 | Hinsken et al. |
| 4,926,190 A | 5/1990 | Laver |
| 4,973,702 A | 11/1990 | Rody et al. |
| 5,175,312 A | 12/1992 | Dubs et al. |
| 5,216,052 A | 6/1993 | Nesvadba et al. |
| 5,252,643 A | 10/1993 | Nesvadba |
| 5,277,664 A | 1/1994 | Mott |
| 5,356,966 A | 10/1994 | Nesvadba |
| 5,369,159 A | 11/1994 | Nesvadba |
| 6,008,285 A | 12/1999 | Kasemann et al. |
| 6,451,887 B1 * | 9/2002 | Wood ............... C08K 5/3475 524/91 |
| 2010/0113641 A1 | 5/2010 | Laredo |
| 2011/0059033 A1 * | 3/2011 | Kitagawa ............. A61K 8/355 424/60 |
| 2012/0142877 A1 | 6/2012 | Laredo |
| 2012/0302760 A1 | 11/2012 | Preschel et al. |
| 2013/0142737 A1 | 6/2013 | Schlifkeposchalko et al. |

FOREIGN PATENT DOCUMENTS

| | | |
|---|---|---|
| DE | 43 16 622 A1 | 11/1993 |
| EP | 0 057 160 A1 | 8/1982 |
| EP | 0 589 839 A1 | 3/1994 |
| EP | 0 591 102 A1 | 4/1994 |
| EP | 1 291 384 A1 | 3/2003 |
| JP | 8-208628 A | 8/1996 |
| JP | 2000-141875 A | 5/2000 |
| WO | WO 98/56852 A1 | 12/1998 |
| WO | WO 98/56853 A1 | 12/1998 |
| WO | WO 2010/060698 A2 | 6/2010 |
| WO | WO 2010/130752 A2 | 11/2010 |
| WO | WO 2011/086127 A1 | 7/2011 |
| WO | WO 2012/163936 A1 | 12/2012 |

OTHER PUBLICATIONS

Medical Definition of Paint, https://medical-dictionary.thefreedictionary.com/paint, p. 1.*
International Search Report and Written Opinion dated Jan. 15, 2015 in PCT/EP2014/072700 filed Oct. 23, 2014.

* cited by examiner

*Primary Examiner* — Robert T Butcher
(74) *Attorney, Agent, or Firm* — Oblon, McClelland, Maier & Neustadt, L.L.P.

(57) ABSTRACT

The present invention relates the use of a 2-(2-hydroxyphenyl)benzotriazole compound of the formula R(QUV)$_n$ as an UV absorbing agent in coatings.

8 Claims, No Drawings

USE OF 2-(2-HYDROXYPHENYL)BENZOTRIAZOLE COMPOUNDS AS AN UV ABSORBING AGENT IN COATINGS

The invention relates to the use of 2-(2-hydroxyphenyl) benzotriazoles compounds of the formula $R(QUV)_n$ as an UV absorbing agent in coatings and for stabilizing coatings. The invention further relates to a method of stabilizing coatings against the effect of light using said benzotriazole compounds.

Many materials and in particular coatings are exposed to light, heat, and temperature changes (i.e., weathering). This may lead to undesired alterations such as color deviation, loss of gloss or even to cracking and delamination. These alterations are often mainly due to light, in particular UV-light, which leads to photochemically induced degradation reactions. Light stabilization of coatings is therefore crucial in order to maintain their appearance and gloss, which are expected to remain unchanged for many years. The induction of these degradation reactions is prevented by adding a compound that absorbs UV-light. The compound that absorbs UV-light reduces the intensity of UV-light within the coating. However, according to the Lambert-Beer-Law, a significant reduction of UV-Intensity can only be achieved in the part of the coating that is not at the surface. No significant reduction of UV-intensity is achieved at the surface of the coating. Degradation reactions are thus induced at the surface of a coating even if a compound that absorbs UV-light is present. For this reason a HALS (Hindered Amine Light Stabilizer) needs to be added as a complementary stabilizer. In most cases it is a derivative of 2,2,6,6-tetramethylpiperidine. HALS compounds scavenge efficiently free radicals formed at the coating surface, where minor or no protection through the UVA is given. This process has been extensively studied and is essentially a cyclic chain breaking antioxidant process which is known as the Denisov cycle.

EP 280 650 A1 describes the use of benzotriazole derivatives as photoprotecting agents for recording materials for inkjet printing. EP 057 160 A1 discloses 2-(2-hydroxyphenyl)benzotriazoles, their use as UV absorbers and their preparation. U.S. Pat. No. 3,213,058 discloses o-hydroxyphenylbenzotriazoles and their use as UV absorbers in plastics.

WO 2011/086124 discloses benzotriazole compounds of the formula

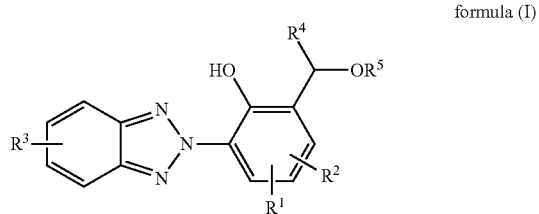

formula (I)

wherein $R^1$ and $R^2$ are hydrogen, $C_{1-30}$alkyl, $C_{1-5}$alkoxy, $C_{1-5}$alkoxycarbonyl, $C_{5-7}$cycloalkyl; $C_{6-10}$aryl or aralkyl; $R^3$ is hydrogen, $C_{1-5}$alkyl, $C_{1-5}$alkoxy, or halogen; $R^4$ is hydrogen, $C_{1-5}$alkyl; and $R^5$ is $C_{1-30}$alkyl or $C_{5-10}$cycloalkyl. The compounds are useful as photostabilizer and solubilizer for dibenzoylmethane derivatives and are used in cosmetic sun care compositions.

WO 2010/130752 describes high molecular non-polar benzotriazoles that are useful of stabilizing plastics against the effect of light.

WO 2011/086127 and WO 2012/163936 describe processes for preparing 2-(2-hydroxyphenyl)benzotriazole compounds.

JP 8-208628 discloses UV absorbers of formula (4)

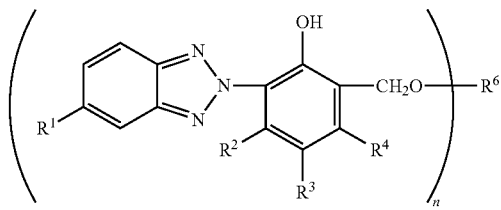

(4)

wherein $R^1$ is hydrogen, halogen, $C_1$-$C_{12}$ alkyl or alkoxy; $R^2$ and $R^4$ are hydrogen, $C_1$-$C_{10}$ alkyl, aryl, aralkyl, alkoxy or phenoxy; $R^3$ is $C_1$-$C_{12}$ alkyl, aryl, aralkyl, alkoxy or phenoxy; $R^6$ is $C_1$-$C_{20}$ alkyl, aryl or aralkyl; and n is an integer of 1 to 4. However, formula (4) is incorrect in that a carbonyl group between the oxygen atom and $R^6$ is missing. This is evident from the preparation method which comprises dissolving a compound of formula (1) (corresponding to formula (4) with $R^6$ being H) and an acid in a suitable solvent and then treating the same by a conventional method at room temperature to reflux temperature, if necessary in the presence of an acid catalyst such as sulfuric acid or methane sulfonic acid. Examples for such acids are acetic acid, propionic acid, butanoic acid, acrylic acid etc. The ether compounds of formula (4) wherein $R^6$ is as defined above cannot be prepared by this method. This is further confirmed by table 1 which refers to compounds of formula (4). However, the compounds given in table 1 are ester compounds rather than ether compounds.

For efficient applicability in coating applications, a light stabilizer has to fulfill a broad range of properties: compatibility with coating formulations of different polarity (i.e. solubility in coating compositions that are based on polar to non-polar solvents, no exudation from the coating), no interference with curing, no impact on the initial color or the initial appearance (e.g. gloss) of the coating, an improvement of resistance towards UV-light that is comparable to established light stabilizers, low volatility, and being liquid under normal conditions, which allows easy incorporation into coating formulations. Broad compatibility along with good solubility in coating formulations of different polarity is a requirement which so far has not been solved.

The problem underlying the invention was therefore to provide light stabilizers that are compatible with, in particular soluble in, coating formulations of different polarity. Furthermore, it is desirable that the light stabilizers meet the other requirements mentioned above as well and in particular provide high light stability.

This problem is solved by the present invention which relates to the use of a 2-(2-hydroxyphenyl)benzotriazole compound of formula I $$R(QUV)_n \qquad (I)$$

as an UV absorbing agent in coatings,
wherein in formula I
R is a mono- to pentadecavalent aliphatic, cycloaliphatic or aromatic group;

UV is a group of the formula II

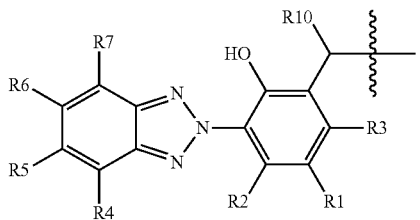

wherein
R1, R2, and R3 which may be the same or different are H, $C_1$-$C_{20}$alkyl, $C_1$-$C_5$alkoxy, $C_1$-$C_5$alkoxycarbonyl, $C_3$-$C_7$cycloalkyl, phenyl, naphthyl or phenyl-$C_1$-$C_5$alkyl;
R4, R5, R6 and R7 which may be the same or different are H, $C_1$-$C_5$alkyl, $C_1$-$C_5$alkoxy, or halogen;
R10 is H or $C_1$-$C_{20}$alkyl;
Q is O;
n is 1, 2, 3, 4, 5, 6, 7, 8, 9, 10, 11, 12, 13, 14 or 15.
Compounds used according to the invention:
According to an embodiment, a compound of formula I is used, wherein R1 is $C_1$-$C_8$alkyl, in particular methyl, and R2 and R3 are H or halogen.
According to a further embodiment, a compound of formula I is used, wherein R4, R5, R6 and R7 are H or halogen.
According to a further embodiment, a compound of formula I is used, wherein R4, R5, R6 and R7 are H or R4 and R7 are H and R5 and R6 are halogen.
According to a further embodiment, a compound of formula I is used, wherein n is 1 and R is selected from:
$C_1$-$C_{20}$alkyl, preferably $C_1$-$C_{18}$alkyl and in particular $C_4$-$C_{12}$alkyl; (R may be a mixture of different alkyl groups, for example a mixture of $C_5$-$C_8$alkyl groups. A compound of formula I with a mixture of such alkyl groups has the advantage of being a liquid);
$C_2$-$C_{20}$alkenyl, preferably $C_2$-$C_6$alkenyl;
$C_1$-$C_{20}$alkylcarbonyl, preferably $C_1$-$C_{18}$alkylcarbonyl;
$C_2$-$C_{20}$alkenylcarbonyl, preferably $C_2$-$C_6$ alkenylcarbonyl;
$C_3$-$C_7$cycloalkyl (preferably cyclopentyl or cyclohexyl) which may be substituted with one, two or three substituents independently selected from $C_1$-$C_5$alkyl, halogen, hydroxy and $C_1$-$C_5$alkoxy; and
-(AO)$_x$—R22, wherein A is —$C_2H_4$—, —$C_3H_6$— or —$C_4H_8$—, preferably —$C_2H_4$— or —$C_3H_6$—, R22 is H, $C_1$-$C_{20}$alkyl or —CO—R24, wherein R24 is $C_1$-$C_{20}$alkyl, and R22 is preferably H or $C_1$-$C_{18}$alkyl and x is 1-20, preferably 1-12 and in particular 1-8.
According to a further embodiment, a compound of formula I is used, wherein n is 1 and R is selected from:
$C_1$-$C_{20}$alkyl, preferably $C_1$-$C_{18}$alkyl and in particular $C_4$-$C_{12}$alkyl; (R may be a mixture of different alkyl groups, for example a mixture of $C_5$-$C_8$alkyl groups. A compound of formula I with a mixture of such alkyl groups has the advantage of being a liquid);
$C_2$-$C_{20}$alkenyl, preferably $C_2$-$C_6$alkenyl;
$C_1$-$C_{20}$alkylcarbonyl, preferably $C_1$-$C_{18}$alkylcarbonyl;
$C_2$-$C_{20}$alkenylcarbonyl, preferably $C_2$-$C_6$ alkenylcarbonyl;
$C_3$-$C_7$cycloalkyl (preferably cyclopentyl or cyclohexyl) which may be substituted with one, two or three substituents independently selected from $C_1$-$C_5$alkyl, halogen, hydroxy and $C_1$-$C_5$alkoxy; and
-(AO)$_x$—R22, wherein A is —$C_2H_4$—, —$C_3H_6$— or —$C_4H_8$—, preferably —$C_2H_4$— or —$C_3H_6$—, R22 is H, $C_1$-$C_{20}$alkyl or —CO—R24, wherein R24 is $C_1$-$C_{20}$alkyl, and R22 is preferably H or $C_1$-$C_{18}$alkyl, and x is 1-20, preferably 1-12 and in particular 1-8;
wherein the following compounds of formula I are excluded in which UV is a group of formula II and $R^2$ and $R^4$, $R^5$, $R^6$, $R^7$ and $R^{10}$ are H and
a) $R^1$ is $CH_3$, $R^3$ is H and R is —$COCH_3$;
b) $R^1$ is t-$C_4H_9$, $R^3$ is H and R is —$COC(CH_3)$=$CH_2$;
c) $R^1$ is $CH_3$, $R^3$ is $CH_3$ and R is —$COCH_3$.
According to a further embodiment, a compound of formula I is used, wherein n is 1 and R is selected from:
$C_1$-$C_{20}$alkyl, preferably $C_1$-$C_{18}$alkyl and in particular $C_4$-$C_{12}$alkyl; (R may be a mixture of different alkyl groups, for example a mixture of $C_5$-$C_8$alkyl groups. A compound of formula I with a mixture of such alkyl groups has the advantage of being a liquid);
$C_2$-$C_{20}$alkenyl, preferably $C_2$-$C_6$alkenyl;
$C_3$-$C_7$cycloalkyl (preferably cyclopentyl or cyclohexyl) which may be substituted with one, two or three substituents independently selected from $C_1$-$C_5$alkyl, halogen, hydroxy and $C_1$-$C_5$alkoxy; and
-(AO)$_x$—R22, wherein A is —$C_2H_4$—, —$C_3H_6$— or —$C_4H_8$—, preferably —$C_2H_4$— or —$C_3H_6$—, R22 is H, $C_1$-$C_{20}$alkyl, or —CO—R24, wherein R24 is $C_1$-$C_{20}$alkyl, and R22 is preferably H or $C_1$-$C_{18}$alkyl and x is 1-20, preferably 1-12 and in particular 1-8.
According to a further embodiment, a compound of formula I is used, wherein n is 2 and R is $C_1$-$C_{20}$alkylene, preferably $C_1$-$C_{12}$alkylene and in particular $C_1$-$C_8$alkylene, $C_2$-$C_{20}$alkenylene, preferably $C_2$-$C_8$alkenylene, —CO—$C_1$-$C_{12}$—CO—, $C_3$-$C_7$cycloalkylene, preferably cyclopentyl or cyclohexyl or
R is -(AO)$_x$-A-, wherein A is $C_2H_4$, $C_3H_6$ or $C_4H_8$, preferably $C_2H_4$ or $C_3H_6$, and x is 1-20, preferably 1-12 and in particular 1-8; and Q is O.
According to a further embodiment, a compound of formula I is used, wherein n is 2 and R is $C_1$-$C_{20}$alkylene, preferably $C_1$-$C_{12}$alkylene and in particular $C_1$-$C_8$alkylene, $C_2$-$C_{20}$alkenylene, preferably $C_2$-$C_8$alkenylene, —CO—$C_1$-$C_{12}$—CO—, $C_3$-$C_7$cycloalkylene, preferably cyclopentyl or cyclohexyl or
R is -(AO)$_x$-A-, wherein A is —$C_2H_4$—, —$C_3H_6$— or —$C_4H_8$—, preferably —$C_2H_4$— or —$C_3H_6$—, and x is 1-20, preferably 1-12 and in particular 1-8; and Q is O;
wherein the following compounds of formula I are excluded in which UV is a group of formula II and $R^2$ and $R^4$, $R^5$, $R^6$, $R^7$ and $R^{10}$ are H and
a) $R^1$ is $OCH_3$, $R^3$ is H and R is —$COCH_2CH_2CO$—;
b) $R^1$ is $CH_3$, $R^3$ is H and R is —$CO(CH_2)_4CO$—;
c) $R^1$ is $CH_3$, $R^3$ is H and R is —$CO(CH_2)_8CO$—.
According to a further embodiment, a compound of formula I is used, wherein n is 2 and R is $C_1$-$C_{20}$alkylene, preferably $C_1$-$C_{12}$alkylene and in particular $C_1$-$C_8$alkylene, $C_2$-$C_{20}$alkenylene, preferably $C_2$-$C_8$alkenylene, $C_3$-$C_7$cycloalkylene, preferably cyclopentyl or cyclohexyl or
R is -(AO)$_x$-A-, wherein A is —$C_2H_4$—, —$C_3H_6$— or —$C_4H_8$—, preferably —$C_2H_4$— or —$C_3H_6$—, and x is 1-20, preferably 1-12 and in particular 1-8; and Q is O.
According to a further embodiment, a compound of formula I in the form of formula Ia is used

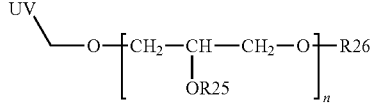

wherein
n is 3, 4, 5, 6, 7, 8, 9, 10, 11, 12, 13, 14 or 15; R25 is H, R23, COR23 or UV and R26 is H, R23, COR23 or UV; R23 is $C_1$-$C_{22}$alkyl or $C_2$-$C_{22}$alkenyl and UV is as defined above. Preferably, n is 5, 6, 7, 8, 9, 10, 11, 12, 13, 14 or 15. According to an embodiment, at least two groups R25 are UV.

The compounds of formula Ia are obtainable by reacting a polyglycerol having 3 to 15 glycerin units wherein one or more of the hydroxyl groups, in particular 1, 2 or 3 hydroxyl groups, may be esterified with a saturated or unsaturated carboxylic acid having 1 to 22 carbon atoms and optionally 1 or 2 double bonds and/or etherified with a $C_1$-$C_{22}$alkyl or $C_2$-$C_{22}$alkenyl group, with a compound of formula (III)

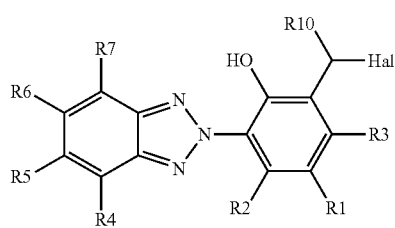

wherein Hal is F, Cl, Br or I, in particular Cl or Br. Preferably, said compound is 2-(2H-benzotriazol-2-yl)-6-(chloromethyl)-4-methyl-phenol.

According to a further embodiment, a compound of formula I is used, wherein n is 1 and R is $C_1$-$C_{20}$alkyl, in particular a mixture of different groups R; or n is 2 and R is $C_1$-$C_{20}$alkylene, -(AO)$_x$-A-.

According to a further embodiment, a compound of formula Ia is used, wherein R25 is H or UV, R26 is H or COR23 and R23, n and UV are as defined above.

The compounds of formula I may be used singly or in admixture of two or more of said compounds.

Compounds of the Invention:

The invention also relates to a compound of formula I

R(QUV)$_n$ (I)

wherein
n is 1 and R is -(AO)$_x$—R22, wherein A is —$C_2H_4$—, —$C_3H_6$— or —$C_4H_8$—, R22 is H, $C_1$-$C_{20}$alkyl, or —CO—R24, wherein R24 is $C_1$-$C_{20}$alkyl, and x is 1-20; or
n is 2 and R is $C_1$-$C_{20}$alkylene, $C_1$-$C_{20}$alkenylene, —CO—$C_1$-$C_{12}$—CO—, $C_3$-$C_7$cycloalkylene, or -(AO)$_x$-A-, wherein A is —$C_2H_4$—, —$C_3H_6$— or —$C_4H_8$—, and x is 1-20; or
n is 3, 4, 5, 6, 7, 8, 9, 10, 11, 12, 13, 14 or 15, in particular 5, 6, 7, 8, 9, 10, 11, 12, 13, 14 or 15 or 5, 6, 7, 8, 9, or 10, and Ra is a tri- to pentadecavalent $C_3$-$C_{40}$alkyl group, in particular penta- to pentadecavalent or decavalent $C_5$-$C_{40}$alkyl group, wherein the alkyl group may be interrupted by oxygen heteroatoms; and Q is O;
UV is a group of the formula II

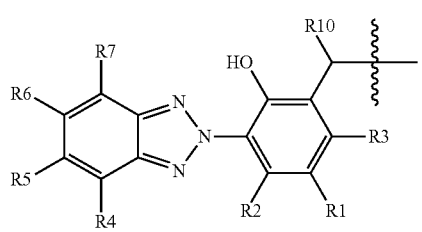

R1, R2, and R3 which may be the same or different are H, $C_1$-$C_{20}$alkyl, $C_1$-$C_5$alkoxy, $C_1$-$C_5$alkoxycarbonyl, phenyl, naphthyl or phenyl-$C_1$-$C_5$alkyl;
R4, R5, R6 and R7 which may be the same or different are H, $C_1$-$C_5$alkyl, $C_1$-$C_5$alkoxy, or halogen;
R$_{10}$ is H or $C_1$-$C_{20}$alkyl;
Q is O;

According to an embodiment, R1 is $C_1$-$C_8$alkyl, in particular methyl, and R2 and R3 are H or halogen.

According to a further embodiment, R4, R5, R6 and R7 are H or halogen.

According to a further embodiment, R4, R5, R6 and R7 are H or R4 and R7 are H and R5 and R6 are halogen.

According to a further embodiment, n is 1 and R is -(AO)$_x$—R22, wherein A is —$C_2H_4$— or —$C_3H_6$—, R22 is H or $C_1$-$C_{20}$alkyl, preferably H or $C_1$-$C_{18}$alkyl and x is 1-20, preferably 1-12 and in particular 1-8.

According to a further embodiment, n is 2 and R is $C_1$-$C_{20}$alkylene, preferably $C_1$-$C_{12}$alkylene and in particular $C_1$-$C_8$alkylene, $C_2$-$C_{20}$alkenylene, preferably $C_2$-$C_8$alkenylene, —$C_3$-$C_7$cycloalkylene, preferably cyclopentyl or cyclohexyl or
-(AO)$_x$—R22, wherein A is —$C_2H_4$—, —$C_3H_6$— or —$C_4H_8$—, preferably —$C_2H_4$— or —$C_3H_6$—, R22 is H or $C_1$-$C_{20}$alkyl, preferably H or $C_1$-$C_{18}$alkyl and x is 1-20, preferably 1-12 and in particular 1-8; and Q is O.

According to a further embodiment, the compound of formula I is in the form of formula Ia

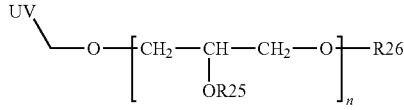

wherein
n is 3, 4, 5, 6, 7, 8, 9, 10, 11, 12, 13, 14 or 15; R25 is H, R23, —COR23 or UV and R26 is H, —COR23 or UV; R23 is $C_1$-$C_{22}$alkyl or $C_2$-$C_{22}$alkenyl and UV is as defined above. Preferably, n is 5, 6, 7, 8, 9, 10, 11, 12, 13, 14 or 15. According to an embodiment, at least two groups R25 are UV.

According to an embodiment of formula Ia, n is 5, 6, 7, 8, 9, 10, 11, 12, 13, 14 or 15; or 5, 6, 7, 8, 9, or 10.

According to a further embodiment of formula Ia, R25 is H or UV, R26 is H or COR23 and R23, n and UV are as defined above.

The compounds of formula Ia are obtainable by reacting a polyglycerol having 3 to 15 glycerin units wherein one or more of the hydroxyl groups, in particular 1, 2 or 3 hydroxyl groups, may be esterified with a saturated or unsaturated carboxylic acid having 1 to 22 carbon atoms and optionally 1 or 2 double bonds or etherified with a $C_1$-$C_{22}$alkyl or $C_2$-$C_{22}$alkenyl group, with a 2-(2H-benzotriazol-2-yl)-6-(chloromethyl) compound of formula (III), in particular 2-(2H-benzotriazol-2-yl)-6-(chloromethyl)-4-methyl-phenol. In the obtained compounds the compound of formula (III) may be attached to all or only a part of the hydroxyl groups. Further, 1 to 3 of the hydroxyl groups, in particular one of the terminal hydroxyl groups, and optionally one or two of the other hydroxyl groups, that are present in the polyglycerol may be esterified with a saturated or unsaturated carboxylic acid having 1 to 22 carbon atoms and optionally 1 or 2 double bonds and/or etherified with a $C_1$-$C_{22}$alkyl or $C_2$-$C_{22}$alkenyl group. Thus, the compound of formula Ia may have, in addition to hydroxyl groups to which the 2-(2H-benzotriazol-2-yl)-6-(chloromethyl)-4-methyl-phenol is attached, free (unreacted) hydroxyl groups and/or esterified hydroxyl groups.

The expressions "alkyl", "alkenyl", "alkoxy", "alkylene". "alkenylene" and "cycloalkylene" used herein have the following meanings:

"Alkyl" (also in "alkoxy" etc.) means a straight chain or branched saturated hydrocarbon group having 1 to 20, for example 1 to 18 or 1 to 12 or 1 to 8 carbon atoms. Examples for alkyl groups are methyl, ethyl, propyl, isopropyl, n-butyl, isobutyl, sec.-butyl, tert.-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethyl pentyl, 1-propylbutyl, n-octyl, 2-ethylhexyl, 2-propylheptyl, 1,1,3,3-tetramethylbutyl, nonyl, decyl, n-undecyl, n-dodecyl, n-tridecyl, iso-tridecyl, n-tetradecyl, n-hexadecyl, n-octadecyl, n-eicosyl, etc.

"Alkenyl" means a straight chain or branched unsaturated hydrocarbon group having 2 to 20, for example 1 to 18 or 1 to 12 or 1 to 8 or 1 to 5 carbon atoms and one or two double bonds. Examples for alkenyl groups are vinyl, allyl, butenyl.

$C_3$-$C_7$cycloalkyl means a saturated cyclic hydrocarbon having 3 to 7 ring carbon atoms. Examples for cycloalkyl groups are cyclopropyl, cyclobutyl, cyclopentyl or cyclohexyl with cyclopentyl and cyclohexyl being preferred.

"Alkylene" and "alkenylene" are divalent alkyl or alkenyl groups and are as defined above.

Processes for preparing the compounds of formula I and Ia are described in great detail in WO 200/086124, WO 2011/086127 and WO 2012/163936. The compounds of formula I and Ia can be prepared according to these methods or in analogy to these methods. The preparation methods of WO 200/086124, WO 2011/086127 and WO 2012/163936 are incorporated into the present application in their entirety.

The starting materials which are reacted with 2-(2H-benzotriazol-2-yl)-6-(chloromethyl)-4-methyl-phenol are in general monoalkanols or a mixture thereof, alkandiols or a mixture thereof, polyols having 3 to 15 hydroxyl groups, polyalkyleneglycols, such as polyethylene glycol or polypropylene glycol, polyglycerol, polyglycerol that is partially esterified with a saturated or unsaturated $C_1$-$C_{20}$carboxylic acid, polyetherpolyols, polyesterpolyols, amines, thiols, diamines, dithiols, polyamines and polythiols. As monoalcohols linear or branched, primary or secondary alkanols, in particular $C_4$-$C_9$ alkanols, or a mixture thereof are used.

Examples for alkanols are 2-ethylhexanol, a mixture of linear and branched hexanols and a mixture of $C_5$-$C_8$ alkanols. As diols linear or branched $C_2$-$C_9$ alkandiols are preferably used. Examples for diols are glycol, 1,2- and 1,3-propanediol, 1,4-butanediol or 1,6-hexanediol. As polyols glycerol, sorbitol or neopentylglycol is preferably used. The polyglycerol preferably includes 2 to 15 glycerol units, in particular 2 to 12 glycerol units. Examples for polyglycerols are diglycerol, triglycerol, hexaglycerol or decaglycerol. The polyglycerol may include regioisomers. Examples for polyglycerol that is partially esterified with a saturated or unsaturated $C_1$-$C_{20}$carboxylic acid are triglycerol monooleate, triglycerol dioleate, triglycerol trioleate, hexaglycerol monooleate, hexaglycerol trioleate, hexaglycerol hexaoleate, decaglycerol monooleate, decaglycerol dioleate, decaglycerol decaoleate, decaglycerol monostearate, and decaglycerol monolaurate.

The compounds of formula I and Ia wherein R is the residue of a polyalkylene glycol or polyglycerol or partially esterified polyglycerol can be prepared by reacting the polyalkylene glycol or polyglycerol or a partially esterified polyglycerol with 2-(2H-benzotriazol-2-yl)-6-(chloromethyl)-4-methyl-phenol in the presence of a base, such as calciumoxide. Preferably, polyalkylene glycol or polyglycerol or partially esterified polyglycerol are used in stoichiometric amounts or in a molar excess of about 10 to 20%. When using partially esterified polyglycerol only a part of the available hydroxyl groups will react with the benzotriazole compound so that unreacted hydroxyl groups may be present in the product. The reaction is preferably carried out in an inert solvent such as a hydrocarbon, for example toluene.

The compounds of formula I are useful as UV absorbing agents. Therefore, they can be used to stabilize organic material against the effects of light.

Preferably, the organic material is a natural, semi-synthetic or synthetic polymer, a binder or a crosslinkable binder of a coating composition or the crosslinked coating.

The compounds of formula I are applied as a composition, in particular as a coating composition, i.e. the organic material is suitable for coating purposes. The composition may be solvent based or water based. Typical examples of organic solvents are aliphatic, aromatic or cycloaliphatic hydrocarbons, alcohols, glycols, esters, acetates and ketones. In another embodiment, the composition is an automotive coating composition.

The coating composition is preferably a laquer, in particular a stoving laquer which is used for coating automobiles (automobile finishing lacquers), for example stoving lacquers comprising alkyd/melamine resins and alkyd/acrylic/melamine resins (see H. Wagner and H. F. Sarx, "Lackkunstharze" (1977), pages 99-123), epoxy/carboxy resins, isocyanate crosslinked acrylic polyols or polyester polyols. Other crosslinking agents include glycoluril resinsor blocked isocyanates.

The coating composition may also comprise an epoxy, epoxy-polyester, vinyl, alkyd, acrylic and polyester resin, optionally modified with silicon, isocyanate or isocyanurate (non-acid catalyzed thermoset resins). The epoxy and epoxy-polyester resins are crosslinked with conventional crosslinkers such as acids, acid anhydrides or amines. Correspondingly, epoxide may be utilized as the crosslinking agent for various acrylic or polyester resin systems that have reactive groups on the backbone structure.

A specific coating composition of the present invention is a radiation curable composition comprising ethylenically unsaturated monomers or oligomers and a polyunsaturated aliphatic oligomer.

Of particular interest is the use of the present compounds as stabilizers for coatings, for example for paints. The invention therefore also relates to those compositions whose component (a) is a film-forming binder for coatings and component (b) is the stabilizer of present invention.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates. Substrates to be coated include wood, ceramic materials, metals, plastics, or articles coated or stained with organic materials.

The binder (component (a)) can in principle be any binder which is customary in industry, for example those described in Ullmann's Encyclopedia of Industrial Chemistry, 5th Edition, Vol. A18, pp. 368-426, VCH, Weinheim 1991. In general, it is a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component (a) can be a cold-curable or hot-curable binder; the addition of a curing catalyst may be advantageous. Suitable catalysts which accelerate curing of the binder are described, for example, in Ullmann's Encyclopedia of Industrial Chemistry, Vol. A18, p. 469, VCH Verlagsgesellschaft, Weinheim 1991.

Preference is given to coating compositions in which component (a) is a binder comprising a functional acrylate resin and a crosslinking agent.

Examples of coating compositions containing specific binders are:

1. paints based on cold- or hot-crosslinkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. two-component polyurethane paints based on thiol-containing acrylate, polyester or polyether resins and aliphatic or aromatic isocyanates, isocyanurates or polyisocyanates;
4. one-component polyurethane paints based on blocked isocyanates, isocyanurates or polyisocyanates which are deblocked during baking, if desired with addition of a melamine resin;
5. one-component polyurethane paints based on aliphatic or aromatic urethanes or polyurethanes and hydroxyl-containing acrylate, polyester or polyether resins;
6. one-component polyurethane paints based on aliphatic or aromatic urethaneacrylates or polyurethaneacrylates having free amino groups within the urethane structure and melamine resins or polyether resins, if necessary with curing catalyst;
7. two-component paints based on (poly)ketimines and aliphatic or aromatic isocyanates, isocyanurates or polyisocyanates;
8. two-component paints based on (poly)ketimines and an unsaturated acrylate resin or a polyacetoacetate resin or a methacrylamidoglycolate methyl ester;
9. two-component paints based on carboxyl- or amino-containing polyacrylates and polyepoxides;
10. two-component paints based on acrylate resins containing anhydride groups and on a polyhydroxy or polyamino component;
11. two-component paints based on acrylate-containing anhydrides and polyepoxides;
12. two-component paints based on (poly)oxazolines and acrylate resins containing anhydride groups, or unsaturated acrylate resins, or aliphatic or aromatic isocyanates, isocyanurates or polyisocyanates;
13. two-component paints based on unsaturated polyacrylates and polymalonates;
14. thermoplastic polyacrylate paints based on thermoplastic acrylate resins or externally crosslinking acrylate resins in combination with etherified melamine resins;
15. paint systems based on siloxane-modified or fluorine-modified acrylate resins;
16. paint systems, especially for clearcoats, based on malonate-blocked isocyanates with melamine resins (e.g. hexamethoxymethylmelamine) as crosslinker (acid catalyzed);
17. UV-curable systems based on oligomeric urethane acrylates and/or other acrylates, if desired in combination with other oligomers or monomers;
18. dual cure systems, which are cured first by heat and subsequently by UV or electron irradiation, or vice versa, and whose components contain ethylenic double bonds capable to react on irradiation with UV light in presence of a photoinitiator or with an electron beam.

Coating systems based on siloxanes are also possible, e.g. systems described in WO 98/56852, WO 98/56853, DE-A-2914427 or DE-A-4338361.

A specific coating composition of the present invention is a powder coating composition.

Particularly preferred coating compositions comprise at least one additive selected from 2-(2'-hydroxyphenyl)benzotriazoles other than that of formula I or Ia, 2-(2-hydroxyphenyl)-1,3,5-triazines, 2-hydroxybenzophenones, and oxanilides.

In the composition, the compound having the formula (I) is in general present in an amount from 0.01 to 30%, 0.02% to 20%, preferably from 0.1% to 10% and more preferably from 0.25% to 5% by weight, based on the weight of the based on the solids content (polymer or resin solids) of the coating composition.

Additionally the coating composition may comprise at least one further additive; examples of additives are listed below:

0. (Hindered Amine Light Stabilizers (HALS)

Preferred HALS compounds are those that are available under the trade names Chimassorb®, Tinuvin®, Hostavin® and Uvinul®. Examples are Chimassorb® 119 FL, 2020, or 940, Tinuvin® 111, 292, 123, 144, 152, 492, 494, 622, 765, 770, 783, 791 or C353, Hostavin® 3050, 3051, 3052, 3055, 3058, PR 31, and Uvinul® 4050 H, 4077 H, or 5050 H.

1. Antioxidants 1.1 Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1-yl)phenol, 2,4-dimethyl-6-(1'-methylheptadec-1'-yl)phenol, 2,4-dimethyl-6-(1'-methyltridec-1-yl)phenol and mixtures thereof.

1.2 Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecyl-thiomethyl-4-nonylphenol.

1.3 Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4 Tocopherols, for example α-tocopherol, β-tocopherol, γ-tocopherol, δ-tocopherol and mixtures thereof (vitamin E).

1.5 Hydroxylated thiodiphenyl ethers, for example 2,2'-thiobis(6-tert-butyl-4-methyl-phenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6 Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7 O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-di methyl benzyl)dithioterephthalate, bis(3,5-di-tert-butyl-4-hydroxybenzyl)sulfide, isooctyl-3,5-di-tert-butyl-4-hydroxybenzylmercaptoacetate.

1.8 Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9 Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-d i-tert-butyl-4-hydroxybenzyl)phenol.

1.10 Triazine derivatives, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11 Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12 Acylaminophenols, for example 4-hydroxylauranilide, 4-hydroxystearanilide, octyl N-(3,5-di-tert-butyl-4-hydroxyphenyl)carbamate.

1.13 Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15 Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16 Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N, N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17 Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18 Ascorbic acid (vitamin C)

1.19 Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluene-sulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octa-decanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenyl-amino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenyl-amines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV absorbers and light stabilizers 2.1 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxy-phenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

[R—CH$_2$CH$_2$—COO—CH$_2$CH$_2$$\overline{)_2}$—, where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl] benzotriazole, 6-butyl-2-[2-hydroxy-3-(1-methyl-1-phenylethyl)-5-(1,1,3,3-tetramethylbutyl)phenyl]-pyrrolo[3,4-f]benzotriazole-5,7(2H,6H)-dione.

2.2 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3 Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butyl-phenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4 Acrylates, for example ethyl α-cyano-6,6-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β, β-diphenylacrylate.

2.5 Nickel compounds, for example nickel complexes of 2,2'-thio-bis[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Other sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxo-spiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)-oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis-[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)-amino)-s-triazine, symmetric diesters of hydroxyalkyl-4-hydroxy-tetraalkylpiperidine compounds such as 2,2,6,6-tetramethyl-1-[2-(3,5,5-trimethyl-hexanoyloxy)-ethyl]-piperidin-4-yl ester.

2.7 Oxanilides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo[triethyltris (3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of □γ-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

10. Other additives, for example plasticizers, lubricants, emulsifiers, pigments, rheology additives, catalysts, flow-control agents, optical brighteners, flame retardants, antistatic agents and blowing agents.

11. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxy-ethoxy) phenyl]benzofuran-2-one, 3,3'-bis[5,7-di-tert-butyl-3-(4-[2- hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctyl-benzofuran-2-one.

The further additives are in general used in an amount of 0.01 to 10% by weight, 0.1 to 8% by weight, and in particular 0.2 to 5% by weight.

The following examples illustrate the invention.

EXAMPLE 1

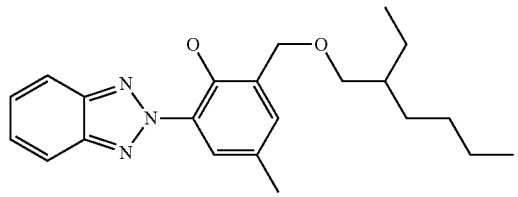

Compound 1

The compound is prepared as described in WO2012163936.

EXAMPLE 2

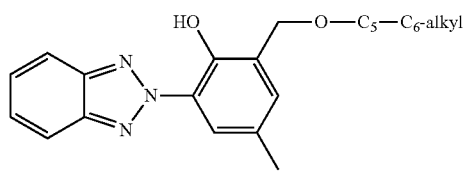

Compound 2

The compound is prepared according to WO2012163936, example 2. 2-Ethyl-hexanol is replaced by a mixture of isomeric C5-C8 alcohols. The product is a waxy solid.

| UV (dioxane) | |
|---|---|
| Wavelength (nm): | E (1%, 1 cm) |
| 343 | 435 |
| 306 | 381 |
| 320 | 329 |
| 340 | 431 |
| 360 | 305 |
| 303 | 385 |

EXAMPLE 3

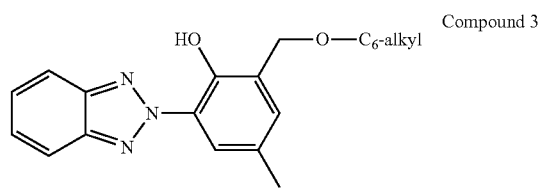

Compound 3

The compound is prepared according to WO2012163936 example 2. 2-Ethyl-hexanol is replaced by a mixture of isomeric C6 alcohols. The product is a colorless liquid.

| UV (dioxane) | |
|---|---|
| Wavelength (nm) | E (1%, 1 cm) |
| 343 | 473 |
| 306 | 415 |
| 320 | 358 |
| 340 | 469 |
| 360 | 336 |
| 303 | 419 |

EXAMPLE 4

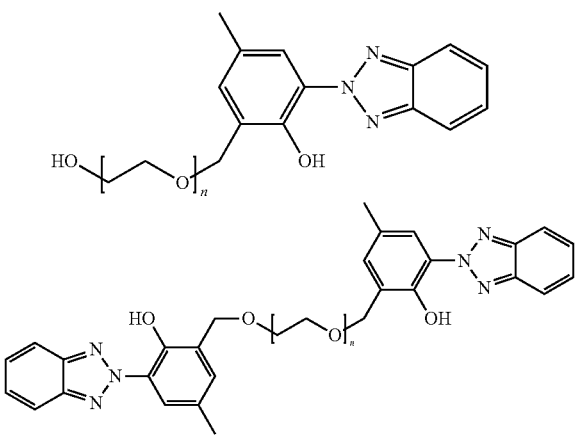

Compound 5

2-(2H-Benzotriazol-2-yl)-6-(chloromethyl)-4-methyl-phenol (prepared as described in WO 2012163936) (15.0 g, 0.055 mol), polyethylene glycol 300 (16.44 g), calcium oxide (3.4 g, 0.060 mol) are suspended in toluene (100 ml) and heated to reflux for 18 h. After cooling to 50° C., the reaction mixture is diluted with ethyl acetate (50 ml) and refluxed for 2 h. The mixture is then filtered and the filtrate is concentrated in vacuo. The residue from the filtrate is redissolved in ethyl acetate (200 ml) and the solvent is completely removed under reduced pressure to give the product as waxy solid (22.5 g).

| UV (dioxane) | |
|---|---|
| Wavelength (nm) | E (1%, 1 cm) |
| 344 | 238 |
| 306 | 193 |
| 320 | 168 |
| 340 | 234 |
| 360 | 179 |
| 303 | 195 |

EXAMPLE 5

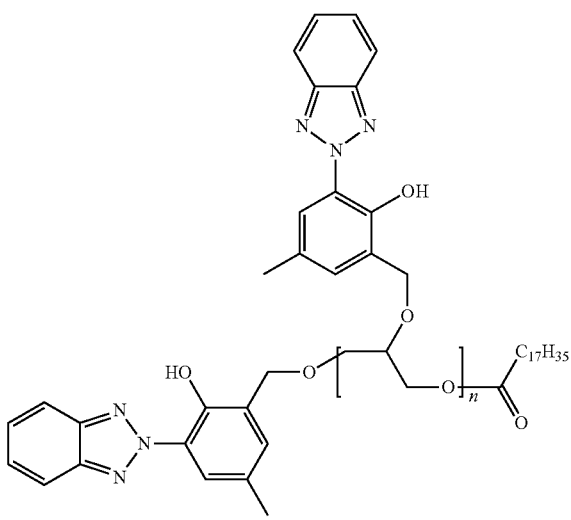

Compound 6

2-(2H-Benzotriazol-2-yl)-6-(chloromethyl)-4-methyl-phenol (15.0 g, 0.055 mol), decaglyceryl stearate (12.0 g), (CAS registry number 79777-30-3) calcium oxide (3.4 g, 0.060 mol) are suspended in toluene (100 ml) and heated to reflux for 18 h. After cooling to 50° C., the reaction mixture is diluted with ethyl acetate (100 ml) and refluxed for 2 h. The mixture is then filtered and the filtrate is concentrated in vacuo. The residue from the filtrate is redissolved in ethyl acetate (300 ml) and the solvent is completely removed under reduced pressure to give the product as waxy solid.

| UV (dioxane) | |
|---|---|
| Wavelength (nm) | E (1%, 1 cm) |
| 343 | 335 |
| 306 | 321 |
| 320 | 269 |
| 340 | 332 |
| 360 | 250 |
| 302 | 325 |

Application Examples

EXAMPLE 6

Stabilization of a 2 Component Polyurethane Coating

The UV absorbers of the present invention are tested in a clear coat having the following composition:

| I. Polyol component | |
|---|---|
| Macrynal SM 510 n (65%)[a] | 75.0 g |
| Butylglycol acetate | 15.0 g |
| Solvesso 100[b] | 6.0 g |
| Methyl isobutyl ketone | 3.6 g |
| Zn - octoate (8% metal) | 0.1 g |
| BYK 300[c] | 0.2 g |
| Subtotal | 100.0 g |
| II. Isocyanate component | |
| Desmodur N 75[d] (75%) | 40.0 g |
| Total | 140.0 g |
| Resin solids (total): | 56.2% |

[a]OH-functional poly(meth)acrylat (Cytec Industries).
[b]aromatic hydrocarbon mixture, boiling range 182-203° C. (Solvesso 150) or 161-178° C. (Solvesso 100); manufacturer: ESSO.
[c]levelling agent based on dimethylpolysiloxane (Byk Chemie, Wesel, Germany).
[d]isocyanate hardener (75% by weight in methoxypropylacetate/xylene 1:1; Bayer Material Science).

2% of the UV absorber to be tested is added to the clear coat, based on the solids content of the paint. The coating formulations are additionally admixed with 1.0% by weight, based on the solids content of the paint, of a co-stabilizer (compound y) with the main component of the formula (Compound y)

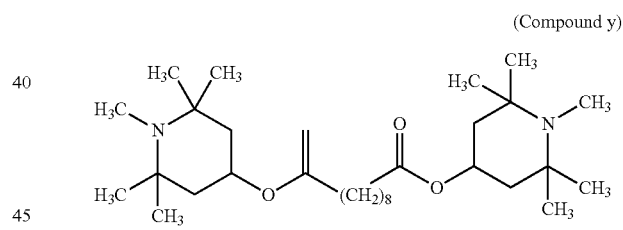

The comparison used is a clear coat containing no light stabilizer.

The clear coat is applied onto a silver metallic base coat resulting after cure (130° C. for 30 minutes) in a dry film thickness of 40 µm.

The samples are subsequently subjected to weathering in an UVCON® weathering device from Atlas Corp. (UVB-313 lamps) with a cycle of 8 h of UV irradiation at 70° C. and 4 h of condensation at 50° C. Further samples are subjected to weathering cycles according to SAE-J 1960 in Xe-WOM weathering device from Atlas Corp.

| | Xenon lamps (SAE J 1960): | | | | | |
|---|---|---|---|---|---|---|
| | gloss (20°) after | | | | | |
| Compound | 0 h | 500 h | 1000 h | 1500 h | 2000 h | 2500 h |
| Without light stabilizer | 93.5 | 85.8 | 62.3 | 63.5 | 52.3 | 53.6 |

-continued

Xenon lamps (SAE J 1960):

| | gloss (20°) after | | | | | |
|---|---|---|---|---|---|---|
| Compound | 0 h | 500 h | 1000 h | 1500 h | 2000 h | 2500 h |
| Example 1 | 93.6 | 92.6 | 93.3 | 93.1 | 92.5 | 91.5 |
| Example 2 | 92.8 | 92.3 | 92.6 | 92.5 | 91.2 | 90.9 |
| Example 3 | 93.5 | 92.4 | 91.8 | 92.3 | 91.9 | 91.1 |
| Example 4 | 93.8 | 90.9 | 90.9 | 91.3 | 88.4 | 88.8 |
| Example 5 | 92.0 | 90.1 | 90.6 | 87.3 | 87.6 | 80.4 |

UVCON® weathering (UVB-313 lamps):

| | gloss (20°) after | | | |
|---|---|---|---|---|
| Compound | 0 h | 500 h | 1000 h | 1250 h |
| Without light stabilizer | 93.5 | 91.8 | 91.7 | 80.6 |
| Example 1 | 93.6 | 93.2 | 92.8 | 92.5 |
| Example 2 | 92.8 | 92.9 | 93.2 | 92.9 |
| Example 3 | 93.5 | 92.1 | 92.3 | 91.7 |
| Example 4 | 93.8 | 92.2 | 93.1 | 91.2 |
| Example 5 | 92.0 | 89.9 | 91.3 | 91.1 |

EXAMPLE 7

Stabilizing an Acrylic/Melamine Coating

The UV absorbers of the present invention are tested in a clear coat having the following composition:

| | |
|---|---|
| Synthacryl® SC 303[1] | 27.51 |
| Synthacryl® SC 370[2] | 23.34 |
| Maprenal® MF 650[3] | 27.29 |
| butyl acetate/butanol (37/8) | 4.33 |
| isobutanol | 4.87 |
| Solvesso® 150[4] | 2.72 |
| Kristallöl K-30 [5] | 8.74 |
| levelling agent Baysilon® MA[6] | 1.20 |
| | 100.00 g |

[1] acrylate resin (65% solution in xylene/butanol 26:9); Cytec Industries
[2] acrylate resin (75% solution in Solvesso 100[4]); Cyte Industries
[3] melamine resin (55% solution in isobutanol); Ineos melamines
[4] aromatic hydrocarbon mixture, boiling range 182-203° C. (Solvesso 150) or 161-178° C. (Solvesso 100); Exxon
[5] aliphatic hydrocarbon mixture, boiling range 145-200° C.; Shell
[6] 1% in Solvesso 150[4]; Borchers 2% of the UV absorber to be tested is added to the clear coat, based on the solids content of the paint. The coating formulations are additionally admixed with 1% by weight, based on the solids content of the paint, of a co-stabilizer (compound z) of the formula

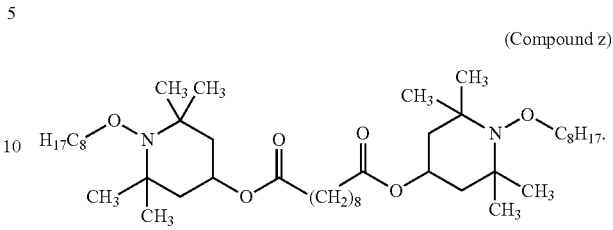

(Compound z)

The comparison used is a clear coat containing no light stabilizer.

The clear coat is reduced to spray viscosity with Solvesso®100 and applied onto a silver metallic base coat resulting after cure (130° C. for 30 minutes) in a dry film thickness of 40 μm.

The samples are subsequently subjected to weathering in an UVCON® weathering device from Atlas Corp. (UVB-313 lamps) with a cycle of 8 h of UV irradiation at 70° C. and 4 h of condensation at 50° C. Another set of samples is subjected to weathering cycles according to SAE-J 1960 in Xe-WOM weathering device from Atlas Corp.

Xenon lamps (SAE J 1960):

| | gloss (20°) after | | | | | | | | |
|---|---|---|---|---|---|---|---|---|---|
| Compound | 0 h | 500 h | 1000 h | 1500 h | 2000 h | 2500 h | 3000 h | 3500 h | 4000 h |
| Without light stabilizer | 92.9 | 89.3 | 81.3 | 61.6 | 24.5 | | | | |
| Example 1 | 93.7 | 92.8 | 92.9 | 92.5 | 92.7 | 92.8 | 91.5 | 90 | 88.8 |
| Example 2 | 91.2 | 90.2 | 93.2 | 93.2 | 92.9 | 92.8 | 92.5 | 92 | 91.5 |
| Example 3 | 92.2 | 91.7 | 92.1 | 91.9 | 92.1 | 92.6 | 92.4 | 92.2 | 92.1 |
| Example 4 | 91.0 | 91.1 | 90.9 | 91.2 | 91.9 | 91.6 | 90.5 | 86.5 | 86.6 |

UVCON® weathering (UVB-313 lamps):

| | gloss (20°) after | | | | |
|---|---|---|---|---|---|
| Compound | 0 h | 500 h | 1000 h | 1500 h | 2000 h |
| Without light stabilizer | 92.9 | 52.2 | 22.7 | | |
| Example 1 | 93.7 | 98.7 | 96 | 96.3 | 95.2 |
| Example 2 | 91.2 | 96.7 | 92.3 | 92.1 | 91.6 |
| Example 3 | 92.2 | 99.6 | 95.3 | 94.2 | 93.0 |
| Example 4 | 91.0 | 96.8 | 87.4 | 88.3 | 83.6 |

EXAMPLE 8

Stabilizing a Clear, Waterborne Wood Coating

The UV absorbers of the present invention are tested in a clear waterborne wood coating based on an acrylic dispersion having the following composition:

| | |
|---|---|
| Water | 18.0 g |
| Ammonia conc. (neutralizing agent) | 0.1 g |
| Byk 346 (wetting agent, Byk Chemie) | 0.1 g |
| FoamStar SI 2280 (defoamer, BASF) | 0.3 g |

-continued

| | |
|---|---|
| Propylene glycol (coalescent agent) | 2.0 g |
| Solvenon DPM (coalescent agent, BASF) | 1.0 g |
| Acronal EDGE 6283 (binder, BASF) | 73.0 g |
| Rheovis PU 1331 (thickener, BASF) | 1.0 g |
| Water | 4.5 g |
| Total | 100.0 g |

Solids content: 31%

2% of the UV absorber to be tested is added in a solution in about 5-10 g of water coalescent mixture to the clear coat, based on the solids content of the paint. The coating formulations are additionally admixed with 1% by weight, based on the solids content of the paint, of a co-stabilizer (compound z) of the formula

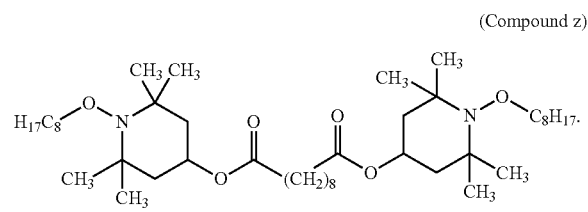

(Compound z)

The co-stabilizer is added in a water-based product form to the formulation.

The comparison used is a clear coat containing no light stabilizer.

The clear coat is applied by brush on pine wood panels. Totally three coats are applied with a drying time of one day between each coat (approximately 80 g/m² per coat resulting in a dry film thickness of approximately 80 μm totally.

The coated wood panels are tested in accelerated weathering equipment (UV-A 340 nm fluorescent lamps; test cycles according to DIN EN 927-6).

| UV-A 340 nm fluorescence bulbs (EN 927-6): | | | | |
|---|---|---|---|---|
| | gloss (60°) after | | | |
| Compound | 0 h | 500 h | 1000 h | 1500 h |
| Without light stabilizer | 62.3 | 43.4 | 39.3 | 36.6 |
| Example 1 | 64.5 | 55.8 | 52.8 | 51.9 |
| Example 2 | 60.9 | 50.4 | 50.6 | 50.9 |
| Example 4 | 63.7 | 52.3 | 45.3 | 42.6 |

The invention claimed is:

1. A method of stabilizing a coating composition comprising a film-forming binder, wherein the coating composition is selected from lacquers, paints for wood, ceramic materials, metals, plastics, or articles coated or stained with organic material, and radiation curable coating compositions, against the effect of light, comprising adding a 2-(2-hydroxyphenyl)benzotriazole compound of formula I $$R(QUV)_m \qquad (I)$$

wherein
UV is a group of formula II

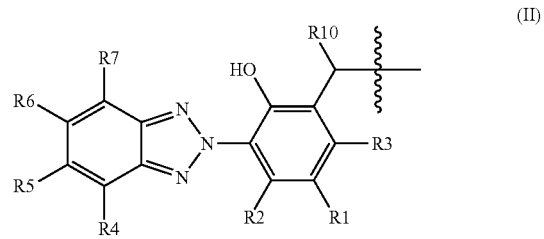

(II)

wherein
R1 is H, $C_1$-$C_{20}$alkyl, $C_1$-$C_5$alkoxy, $C_1$-$C_5$alkoxycarbonyl, $C_3$-$C_7$cycloalkyl, or naphthyl;
R2 and R3 which may be the same or different are H, $C_1$-$C_{20}$alkyl, $C_1$-$C_5$alkoxy, $C_1$-$C_5$alkoxycarbonyl, $C_3$-$C_7$cycloalkyl, phenyl, naphthyl or phenyl-$C_1$-$C_5$alkyl;
R4, R5, R6 and R7 which may be the same or different are H, $C_1$-$C_5$alkyl, $C_1$-$C_5$alkoxy, or halogen;
R10 is H or $C_1$-$C_{20}$alkyl;
Q is O; and
m is 1 and R is selected from $C_1$-$C_{20}$alkyl, $C_2$-$C_{20}$alkenyl, $C_3$-$C_7$cycloalkyl which may be substituted with one, two or three substituents independently selected from $C_1$-$C_5$alkyl, halogen, hydroxy and $C_1$-$C_5$alkoxy; and -(AO)$_x$—R22, wherein A is —$C_2H_4$—, —$C_3H_6$— or —$C_4H_8$—, R22 is H, $C_1$-$C_{20}$alkyl, or —CO—R24, wherein R24 is $C_1$-$C_{20}$alkyl, and x is 1-20;
m is 2 and R is $C_1$-$C_{20}$alkylene, $C_2$-$C_{20}$alkenylene, $C_3$-$C_7$cycloalkylene, or -(AO)$_x$-A-, wherein A is —$C_2H_4$—, —$C_3H_6$— or —$C_4H_8$ and x is 1-20;
to the coating composition.

2. The method according to claim 1, wherein R1 is $C_1$-$C_8$alkyl and R2 and R3 are H or halogen.

3. The method according to claim 1, wherein R4, R5, R6 and R7 are H or halogen.

4. The method according to claim 3, wherein
R4, R5, R6 and R7 are H; or
R4 and R7 are H and R5 and R6 are halogen.

5. The method according to claim 1, wherein in formula I m is 1 and R is $C_1$-$C_{20}$alkyl; or m is 2 and R is $C_1$-$C_{20}$alkylene or -(AO)$_x$-A—.

6. The method according to claim 1, further comprising adding a HALS compound to the coating composition.

7. The method according to claim 6, wherein the HALS compound is at least one selected from the group consisting of bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6- tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine; a condensate of 1,6-hexanediamine and 2,4,6-trichloro-1,3,5-triazine as well as N,N-dibutylamine and 4-butylamino-2,2,6,6-tetramethylpiperidine; N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethy)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor, 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, and 1,3,5-tris(N-cyclohexyl-N-(1,2,2,6,6-pentamethylpiperazine-3-one-4-yl)amino)-s-triazine.

8. The method according to claim 1, wherein in formula I m is 1 and R is a mixture of different $C_1$-$C_{20}$alkyl groups which is such that the compound of formula I is liquid at ambient temperature, $C_2$-$C_{20}$alkenyl, $C_3$-$C_7$cycloalkyl which may be substituted with one, two or three substituents independently selected from $C_1$-$C_5$alkyl, halogen, hydroxyl and $C_1$-$C_5$alkoxy; and -(AO)$_x$—R22, wherein A is —$C_2H_4$—, —$C_3H_6$— or —$C_4H_8$—, R22 is H, $C_1$-$C_{20}$alkyl, or —CO—R24, wherein R24 is $C_1$-$C_{20}$alkyl, and x is 1-20.

* * * * *

UNITED STATES PATENT AND TRADEMARK OFFICE
CERTIFICATE OF CORRECTION

PATENT NO. : 10,119,039 B2  
APPLICATION NO. : 15/026085  
DATED : November 6, 2018  
INVENTOR(S) : Thomas Ehlis et al.

Page 1 of 1

It is certified that error appears in the above-identified patent and that said Letters Patent is hereby corrected as shown below:

In the Specification

Column 5, Line 10 (approx.), "unsatured" should read -- unsaturated --, therefor.

Column 5, Line 26, "CI" should read -- Cl --, therefor.

Column 6, Line 52, "unsatured" should read -- unsaturated --, therefor.

Column 7, Line 19, "ethyl pentyl" should read -- ethylpentyl --, therefor.

Column 8, Line 30, "laquer," should read -- lacquer, --, therefor.

Column 8, Line 31, "laquer" should read -- lacquer --, therefor.

Column 14, Line 5, "6,6" should read -- β,β --, therefor.

Column 16, Line 38, "ocatadecyl-" should read -- octadecyl- --, therefor.

In the Claims

Column 26, Line 8 (approx.), Claim 7, "hydroxyethy)" should read -- hydroxyethyl) --, therefor.

Signed and Sealed this  
Twenty-eighth Day of April, 2020

Andrei Iancu  
*Director of the United States Patent and Trademark Office*